US009375157B2

(12) United States Patent
Kowarschik et al.

(10) Patent No.: US 9,375,157 B2
(45) Date of Patent: Jun. 28, 2016

(54) ANGIOGRAPHIC EXAMINATION METHOD FOR THE REPRESENTATION OF FLOW PROPERTIES

(71) Applicant: Siemens Aktiengesellschaft, München (DE)

(72) Inventors: Markus Kowarschik, Nürnberg (DE); Thomas Redel, Poxdorf (DE)

(73) Assignee: Siemens Aktiengesellschaft, München (DE)

( * ) Notice: Subject to any disclaimer, the term of this patent is extended or adjusted under 35 U.S.C. 154(b) by 98 days.

(21) Appl. No.: 14/027,294

(22) Filed: Sep. 16, 2013

(65) Prior Publication Data

US 2014/0094680 A1    Apr. 3, 2014

(30) Foreign Application Priority Data

Sep. 28, 2012   (DE) .......................... 10 2012 217 792

(51) Int. Cl.
*A61B 5/026* (2006.01)
*A61B 6/00* (2006.01)

(52) U.S. Cl.
CPC .............. *A61B 5/026* (2013.01); *A61B 6/4458* (2013.01); *A61B 6/4464* (2013.01); *A61B 6/507* (2013.01)

(58) Field of Classification Search
CPC .... A61B 5/026; A61B 6/4458; A61B 6/4464; A61B 6/507
See application file for complete search history.

(56) References Cited

U.S. PATENT DOCUMENTS

| 6,052,476 | A * | 4/2000 | Qian et al. ................... 382/130 |
| 7,500,782 | B2 | 3/2009 | Klingenbeck-Regn |
| 2005/0234349 | A1 * | 10/2005 | Pravica et al. ............... 600/481 |
| 2009/0214097 | A1 * | 8/2009 | Mohamed et al. ........... 382/131 |
| 2011/0002517 | A1 * | 1/2011 | Mollus et al. ................ 382/130 |
| 2011/0037761 | A1 * | 2/2011 | Mistretta et al. ............. 345/419 |
| 2011/0038517 | A1 * | 2/2011 | Mistretta et al. ............. 382/128 |
| 2012/0114217 | A1 * | 5/2012 | Mistretta et al. ............. 382/133 |
| 2013/0281829 | A1 * | 10/2013 | Tan et al. ..................... 600/416 |
| 2013/0303893 | A1 * | 11/2013 | Duindam et al. ............ 600/424 |
| 2014/0313196 | A1 * | 10/2014 | Mistretta et al. ............. 345/424 |

OTHER PUBLICATIONS

Syngo i Flow / Dynamic Flow Evaluation / Answers for life, Siemens AG; Siemens AG, Medical Solutions, Angiography, Fluoroscopic and Radiographic Systems, Order No. A91AX-20902-11C1-7600 | Printed in Germany | CC AX WS 12081.5 | © 12.2008, Siemens AG; 2008.
Charles Anthony Mistretta, E. Oberstar, B. Davis, E. Brodsky, C.M. Strother; 4D-DSA and 4D Fluoroscopy: Preliminary Implementation, Proceedings of the SPIE—The International Society for Optical Engineering: 2010. vol. 7622, pp. 762227-1 to 762227-8 (8 pp.), Conference: San Diego, CA, USA, Feb. 15-18, 2010, Conference paper (English); 2010.

(Continued)

*Primary Examiner* — Baisakhi Roy

(57) ABSTRACT

An angiographic examination method for the representation of flow properties of vessels of an object under examination is presented. To determine blood-flow parameters in 3-D with high temporal resolution, at least one 4-D DSA sequence is acquired for the generation of measurement-based 4-D DSA data sets. A model-based method determines time-dependent volume data sets, which, in terms of time, lie between the time-dependent volume data sets of the measurement-based 4-D DSA method.

4 Claims, 5 Drawing Sheets

(56) References Cited

OTHER PUBLICATIONS

Charles Anthony Mistretta; Sub-Nyquist acquisition and constrained reconstruction in time resolved angiography, Med. Phys. vol. 38, Issue 6, Jun. 2011, Am. Assoc. Phys. Med. pp. 2975-2985; 2011.

Juergen Endres, Thomas Redel, Markus Kowarschik, Jana Huller, Joachim Hornegger, Arnd Doerfler, Virtual Angiography using CFD Simulations based on Patient-Specific Parameter Optimization, 9th IEEE International Symposium on Biomedical Imaging (ISBI), May 2-5, 2012; pp. 1200-1203; 2012.

* cited by examiner

ANGIOGRAPHIC EXAMINATION METHOD FOR THE REPRESENTATION OF FLOW PROPERTIES

CROSS REFERENCE TO RELATED APPLICATIONS

This application claims priority to German application No. 10 2012 217 792.2 DE filed Sep. 28, 2012, the entire content of which is hereby incorporated herein by reference.

FIELD OF INVENTION

The invention relates to an angiographic examination method for the representation of flow properties of vessels of an object under examination.

BACKGROUND OF INVENTION

An examination method of this kind can, for example, be used when performing digital subtraction angiography (DSA) and is known from U.S. Pat. No. 7,500,784 B2 which is explained below with reference to FIG. 6.

The quantification of blood flow on the basis of image data during an intervention is a clinically relevant problem. For example, the measurement of blood flow rates in a blood vessel (for example expressed in ml/min) on the basis of X-ray images could be used to evaluate interventional treatment of stenoses for example in cerebral or in peripheral vessels in the catheter laboratory and hence to provide the doctor with information on the outcome of the therapy. Therefore, the doctor could, for example, determine whether the reopening of an occluded vessel by means of a balloon or the implantation of a stent has resulted in an increase in the blood-flow rate to the desired degree.

Invasive possibilities for the measurement of blood flow already exist and are already in clinical use. One example of a method is the use of thermodilution catheters, which are introduced into the blood vessel to be examined. During thermodilution, a specific volume of a cooled solution is injected intravenously. The cold liquid passes through the right half of the heart, then the lung and the left half of the heart, following which it enters the systemic circulation. At a measuring point, the temperature of the blood is determined and a so-called thermodilution curve recorded. However, in terms of the workflow, this technology is complicated, expensive, relatively inaccurate and only suitable for sufficiently large vessels. There are also ultrasound-based invasive measuring probes, which have to be applied from the exterior onto the blood vessel to be examined, i.e. require an open surgical intervention, and are hence often not practicable.

Non-invasive possibilities include blood-flow measurements using magnetic resonance imaging (MRI) technology, for example, based on phase-contrast MRI. Computed tomography scanning also enables flow determinations in the context of perfusion imaging to some extent. However, these approaches are generally not suitable for interventional techniques, i.e. while a patient is being treated in a catheter laboratory.

There are also some non-invasive techniques based on ultrasound, for example Doppler ultrasound, which, although they can be used in interventional procedures, are relatively imprecise and also require a good acoustic window, which, in particular in the case of intracranial vessels is frequently difficult.

SUMMARY OF INVENTION

The invention is based on the question as to which X-ray image-based approaches can be used in interventional procedures involving a C-arc system.

Nowadays, products available for interventional procedures for the representation of flow properties of cerebral vessels are exclusively based on two-dimensional image sequences. In such cases, 2-D DSA sequences are recorded with a high image frequency and the course of the contrast medium analyzed on a pixel-by-pixel basis. Suitable temporal flow parameters are calculated from the time-contrast curve produced in this way and depicted in color. The software 'syngo iFlow' produced by Siemens AG, Healthcare Sector, follows this principle and encodes the time-to-peak parameter of the contrast medium for color-coded representation, as may be derived from the brochure "syngo iFlow/Dynamic Flow Evaluation/Answers for life", Order No. A91AX-20902-11C1-7600, print reference CC AX WS 12081.5, 12.2008, from Siemens AG, Medical Solutions, Angiography, Fluoroscopic and Radiographic Systems. However, as is known, the projective mapping causes the 2-D imaging to lack depth and hence be subject to disruptive superimposition effects resulting from complex vascular geometries, for example, in the brain.

Methods for blood flow quantification in 3-D are the subject matter of current research. It is possible to differentiate the approaches in existence to date from the number of physical model assumptions on which they are based.

Methods of numerical flow simulation (CFD=computational fluid dynamics) are based on the fact that the flow behavior of the blood is described by using mathematical equations, for example by means of Navier-Stokes equations. These equations are resolved by numerical simulation. In this case, the required boundary conditions, such as the vascular geometry, the patient's pulse rate etc., can be obtained from previously acquired image data. These can be 2-D DSA series with high temporal resolution or 3-D DSA images without temporal information. Depending upon the type of modeling, the solution to these equations results in a plurality of physical flow parameters such as flow rate, blood pressure, wall shear forces, etc. These parameters are each typically both position-dependent and time-dependent.

FIG. 1 shows an example of a distribution of wall shear forces in an aneurysm at a vascular bifurcation at a time during the heart cycle calculated by a CFD (computational fluid dynamics) method. The CFD calculation reveals regions with low wall shear forces 16 and regions with high wall shear forces 17. A scale of the wall shear forces 18 is used to obtain an estimation of the values that occur.

Contrary to these model-based approaches, the method 4-D DSA developed by Prof. Dr. Charles A. Mistretta et al. in "4D DSA and 4D Fluoroscopy: Preliminary Implementation", Proceedings of the SPIE—The International Society for Optical Engineering, 2010, Vol. 7622, pages 762227-1 to 8, was proposed in 2010; this functions purely on an image basis and without making any model assumptions. This has the advantage that no generalizing or simplifying model assumptions need to be used in order to determine information with respect to the blood flow.

However, contrary to model-based approaches, such as, for example, CFD methods, the abovementioned 4-D DSA is not able to provide complex physical flow parameters, such as, for example, blood pressures. On the other hand, this method only provides temporal information on the contrast-medium passage in 3-D (i.e. similarly to syngo iFlow in 2-D) which enables estimations of flow rates, from which it is then in turn possible in a subsequent computing step to estimate volumetric flow rates using 3-D geometry information such as the vascular diameters.

The idea behind the 4-D DSA approach consists in the extraction of the dynamic behavior of the contrast medium in the vessels from the projections of rotation angiography and the superimposition thereof in a static 3-D image of the vascular tree by means of perspective back projection. This results in a temporally resolved series of 3-D data sets; each time of these series has a volume data set, which represents the filling of the vascular tree with contrast medium at the respective time. To compensate superimposition effects approximately, back projections from a plurality of directions are used for each time-dependent 3-D data set to be calculated and this obviously results in a loss of temporal resolution. From a purely theoretical view, the 4-D DSA method is based on the question as to whether previous 3-D knowledge, a static 3-D image, into which a back projection is inserted, can be used to violate the scanning theorem while still determining clinically usable image data with sufficiently high temporal resolution.

This procedure is illustrated in FIG. 2 and is explained in more detail below. Section V of the article "Sub-Nyquist acquisition and constrained reconstruction in time resolved angiography" by C. A. Mistretta in Medical Physics 2011 describes how the temporal information of the acquired projections from the angular interval of $\theta$ to $\theta+\Delta\theta$ is used in order to calculate a time-dependent volume data set.

FIGS. 3 to 5 show a sequence of DSA X-ray images which are intended to illustrate the use of the 4-D DSA method. Each X-ray image of this kind, which will hereinafter be referred to as a DSA volume image, corresponds to a time and was obtained by forward projection of the 3-D data set belonging to this time. The first images in the series (starting at the top left) only show the arterial influence of the contrast medium, while in the last images in the series (ending at the bottom right), it is already possible to identify the venous discharge of the contrast medium.

FIG. 3 shows a first DSA volume image 20 with a vascular tree 21 viewed from an angle. In a first region 22, the vascular tree 21 has strong opacity, in a second region 23 weak opacity and in two further regions 24 and 25 no opacity at all since the contrast medium has only penetrated the part of the vascular tree 21 shown in FIG. 4 to a small degree.

FIG. 4 shows a second DSA volume image 26 at a later time from the same view as the DSA volume image 20, in which the first region 22 of the vascular tree 21 has very strong opacity, the second region 23 has strong opacity, the third region 24 has weak opacity and the fourth region 25 has no opacity so that it may be identified that the contrast medium has advanced further in the vascular tree 21.

FIG. 5 now shows a third DSA volume image 27 in which the contrast medium has penetrated very far so that it almost fills the entire vascular tree 21. The first region 22 of the vascular tree 21 has full opacity, the second region 23 has very strong opacity, the third region 24 has strong opacity and the fourth region 25 has weak opacity.

One problem with the 4-D DSA method is that, in the case of complex vascular geometries, the contrast-medium dynamics can only be acquired very poorly, i.e. only with very low temporal resolution. This is due to the complex superimposition effects which make it difficult to identify and extract the flow behavior in individual vascular sections in the projections of the basic rotation angiography. Therefore, with respect to the above depiction, a very high $\Delta\theta$ is required.

However, when using 4-D DSA, it is desirable to maintain a temporal resolution which is not significantly below the very high temporal resolution of a 2-D DSA series. 2-D DSA imaging currently achieves image repetition rates of 30/sec.

An angiographic examination method such as that described above can, for example, be performed with an angiography system known from U.S. Pat. No. 7,500,784 B2, which is explained in the following.

FIG. 6 shows an exemplary biplanar X-ray system with two C-arms 2 and 2' each held by a stand 1 and 1' in the form of a six-axis industrial or buckling-arm robot, wherein an X-ray source, for example X-ray emitters 3 and 3' with X-ray tubes and collimators and an X-ray image detector 4 and 4' as an image capturing unit are attached to each of the ends of the C-arms. Here, the stand 1 is mounted on the floor 5 while the second stand 1' can be fixed to the ceiling 6.

The buckling-arm robot known, for example from U.S. Pat. No. 7,500,784 B2, which preferably has six axes of rotation and hence six degrees of freedom, can be used for the spatial adjustment of the C-arms 2 and 2' at will, for example, by rotating them about their centers of rotation between the X-ray emitters 3 and 3' and the X-ray image detectors 4 and 4'. The angiographic X-ray system 1 to 4 according to the invention can in particular be rotated about centers of rotation and axes of rotation in the C-arm plane of the X-ray image detectors 4 and 4', preferably about the center point of the X-ray image detectors 4 and 4' and about axes of rotation intersecting the center point of the X-ray image detectors 4 and 4'.

The known buckling-arm robot has a base frame, which, for example, is fixed to the floor 5 or the ceiling 6. A turntable is attached thereto so as to be capable of rotating about a first axis of rotation. A robot rocker capable of swiveling about a second axis of rotation is attached to the turntable wherein a robot arm capable of rotating about a third axis of rotation is attached to said rocker. A robot hand is attached to the end of the robot arm so as to be capable of rotating about a fourth axis of rotation. The robot hand has a fixing element for the C-arm 2 or 2', which is capable of swiveling about a fifth of rotation and capable of rotating about a sixth axis of rotation extending perpendicular thereto.

The implementation of the X-ray diagnostic device is not dependent on the industrial robot. It is also possible to use conventional C-arm devices.

The X-ray image detectors 4 and 4' can be rectangular or square flat semiconductor detectors and are preferably made from amorphous silicon (a-Si). However, it is also possible to use integrating and possibly metering CMOS detectors.

Located in the beam path of the X-ray emitters 3 and 3' there is a table board 7 of a patient support table 8 for receiving a patient to be examined as an object under examination. The patient support table 8 is provided with a control panel 9. Connected to the X-ray diagnostic device is a system control unit 10 with an image system 11, which receives and processes the image signals from the X-ray image detectors 4 and 4' (operating elements are for example not shown). The X-ray images can then be viewed on displays of a bank of monitors 12.

Instead of the exemplary X-ray system shown in FIG. 1 with the stands 1 and 1' in form of the six-axis industrial or buckling-arm robot, it is also possible, as shown in simplified form in FIG. 2 for the angiographic X-ray system to have a normal ceiling- or floor-mounted holder for the C-arms 2.

Instead of the exemplary C-arms 2 and 2' shown, the angiographic X-ray system can also have separate ceiling- or floor-mounted holders for the X-ray emitters 3 and 3' and the X-ray image detectors 4 and 4', which are for example electronically rigidly coupled.

The X-ray emitters 3 and 3' emit beam clusters 12 and 12' originating from beam foci of their X-ray sources which strike the X-ray image detectors 4 and 4'. If 3-D data sets are to be created according to the DynaCT method, the rotatably mounted C-arms 2 and 2' with X-ray emitters 3 and 3' and X-ray image detectors 4 and 4' are rotated such that, as shown schematically in FIG. 2 in a top view of the axis of rotation, the X-ray emitters 3 and 3', here depicted figuratively by their beam foci, and the X-ray image detectors 4 and 4' move in an orbit 15 about an object 14 to be examined located in the beam path of the X-ray emitters 3 and 3'. The orbit 15 can be traversed completely or partially in order to create a 3-D data set.

In this case, the C-arms 2 and 2' with X-ray emitters 3 and 3' and X-ray image detectors 4 and 4' move according to the DynaCT method preferably through an angular range of at least 180°, for example 180° plus a fan angle, and record projection images from different projections in a rapid sequence. The reconstruction can be based on only a subarea of said acquired data.

The object 14 to be examined can, for example, be an animal or human body or even a phantom body.

The X-ray emitters 3 and 3' and the X-ray image detectors 4 and 4' each rotate about the object 14 such that the X-ray emitters 3 and 3' and the X-ray image detectors 4 and 4' are arranged on opposite sides of the object 14.

In normal radiography or fluoroscopy, if necessary, an X-ray diagnostic device of this kind can buffer and/or process the medical 2-D data of the X-ray image detectors 4 and 4' in the image system 8 and then display it on the monitor 9.

At each recording position, 2-D DSA X-ray images are acquired and calculated by means of a known reconstruction method to produce a 3-D DSA volume image.

The invention is based on the object of designing an angiographic examination method for the representation of flow properties of vessels of an object under examination of the type mentioned in the introduction such that 4-D DSA data sets are obtained which enable the quantification of blood flow with high temporal resolution in 3-D, wherein the basic question is which X-ray image based approaches are used in the interventional procedures when using a C-arc system (non-invasive).

According to the invention, the object is achieved for an angiographic examination method of the type mentioned in the introduction by the features disclosed in claim 1. Advantageous embodiments are disclosed in the dependent claims.

According to the invention, the object is achieved in that, for the determination of blood flow parameters in 3-D with high temporal resolution, at least one 4-D DSA sequence for the generation of measurement-based 4-D DSA data sets is acquired, wherein a model-based method determines time-dependent volume data sets, which, in terms of time, lie between the time-dependent volume data sets of the measurement-based 4-D DSA method. This produces 4-D DSA data sets which enable a quantification of blood flow with high temporal resolution in interventional procedures when using a C-arm system.

In an advantageous way, CFD-based interpolation over time is calculated with simplifying and generalizing model assumptions, while the measurement-based method is not based on any simplifying physical and physiological assumptions. This is achieved in that only the patient-specific image material acquired is used as input.

For an angiographic examination method, the object is also achieved by the following steps:
S1) acquisition of a 4-D DSA sequence for the generation of measurement-based 4-D DSA data sets,
S2) reconstruction of a temporally resolved series of 3-D data sets for the generation of the temporal course of a contrast-medium density distribution,
S3) generation of a 3-D data set with complete contrast-medium filling of the vessels to be examined,
S4) definition of a model geometry for a CFD simulation,
S5) calculation of a CFD simulation with prespecified initial boundary conditions and simulation parameters in at least one time interval from $t_j$ to $t_{j+1}$,
S6) simulation of the contrast-medium transport for the generation of a virtual contrast-medium density distribution at the time $t_{j+1}$,
S7) solution of an inverse problem with the aid of the virtual and real contrast-medium density distribution at the times $t_j$ and $t_{j+1}$ of the at least one time interval,
S8) repetition of the method steps 3 and 4 in a subsequent time interval $t_{j+1}$ to $t_{j+2}$, until complete virtual contrast-medium filling of the vascular tree is achieved,
S9) calculation of the contrast-medium density distributions at any interim time points $t_{j,n}$ and
S10) combination of the simulated and calculated contrast-medium density distributions and visualization of this combination.

It has been found to be advantageous if, to solve the inverse problem according to method step S7), an iterative optimization by the adaptation of the degrees of freedom of the CFD simulation is performed until, starting from the initial data of the 3-D data set at the earlier time $t_j$, the simulation leads to the result data of the 3-D data set at the later time $t_{j+1}$.

According to the invention, for further refinement, the degrees of freedom in each method step are optimized for all time intervals calculated up to that time.

BRIEF DESCRIPTION OF THE DRAWINGS

The invention is described in more detail below with reference to exemplary embodiments shown in the drawing, which shows.

DETAILED DESCRIPTION OF INVENTION

Figure 1:
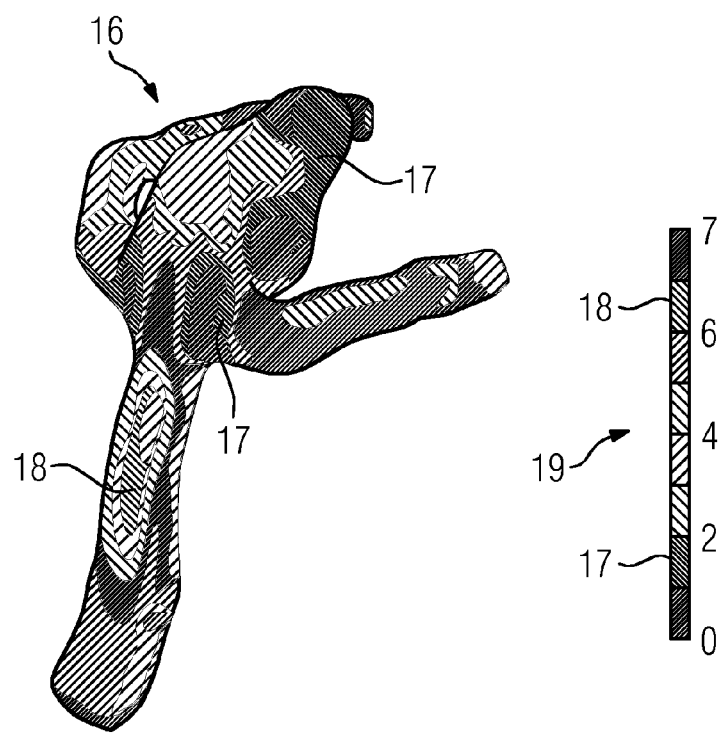
FIG. 1 a representation illustrating the 4-D DSA method,
FIG. 2 a B/W reproduction of a colored distribution of wall shear forces in an aneurysm at a vascular bifurcation,
FIGS. 3 to 5 representations of a sequence of images created using the 4-D DSA method,
FIG. 6 a biplanar C-arm angiography system each with an industrial robot as carrying appliances,
FIG. 7 the sequence of operations of the angiographic examination method according to the invention and
FIG. 8 a representation to illustrate the times of the actually measured and the calculated volume data sets.
Figure 2:
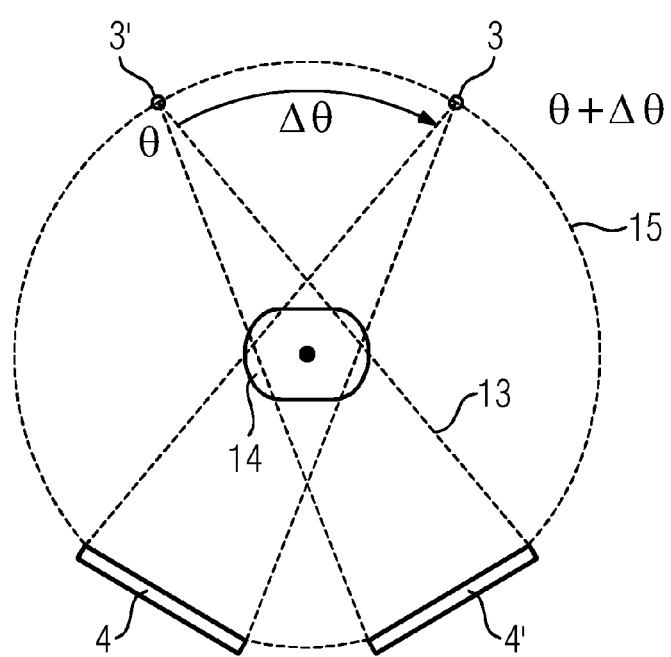
Figure 3:
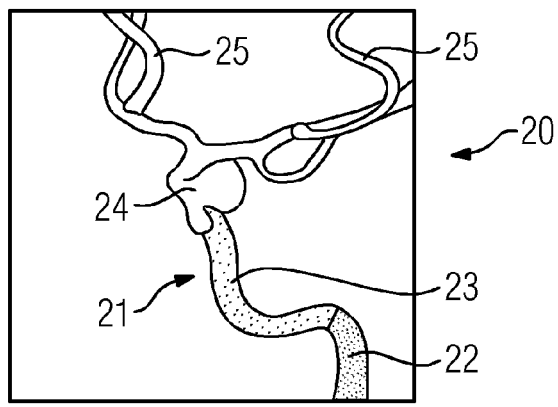
Figure 4:
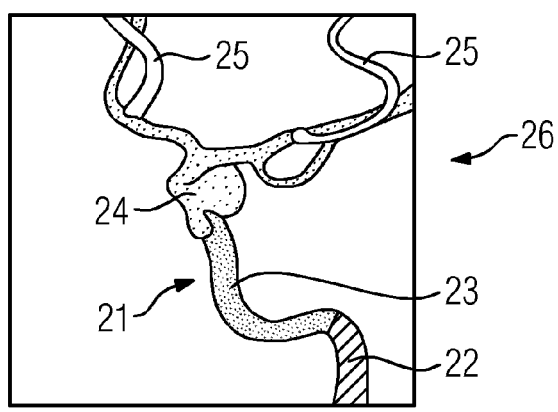
Figure 5:
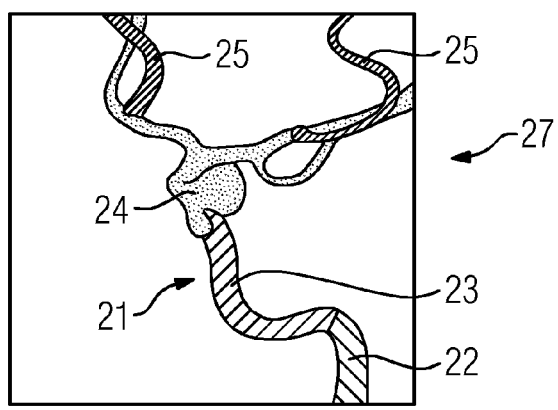
Figure 6:
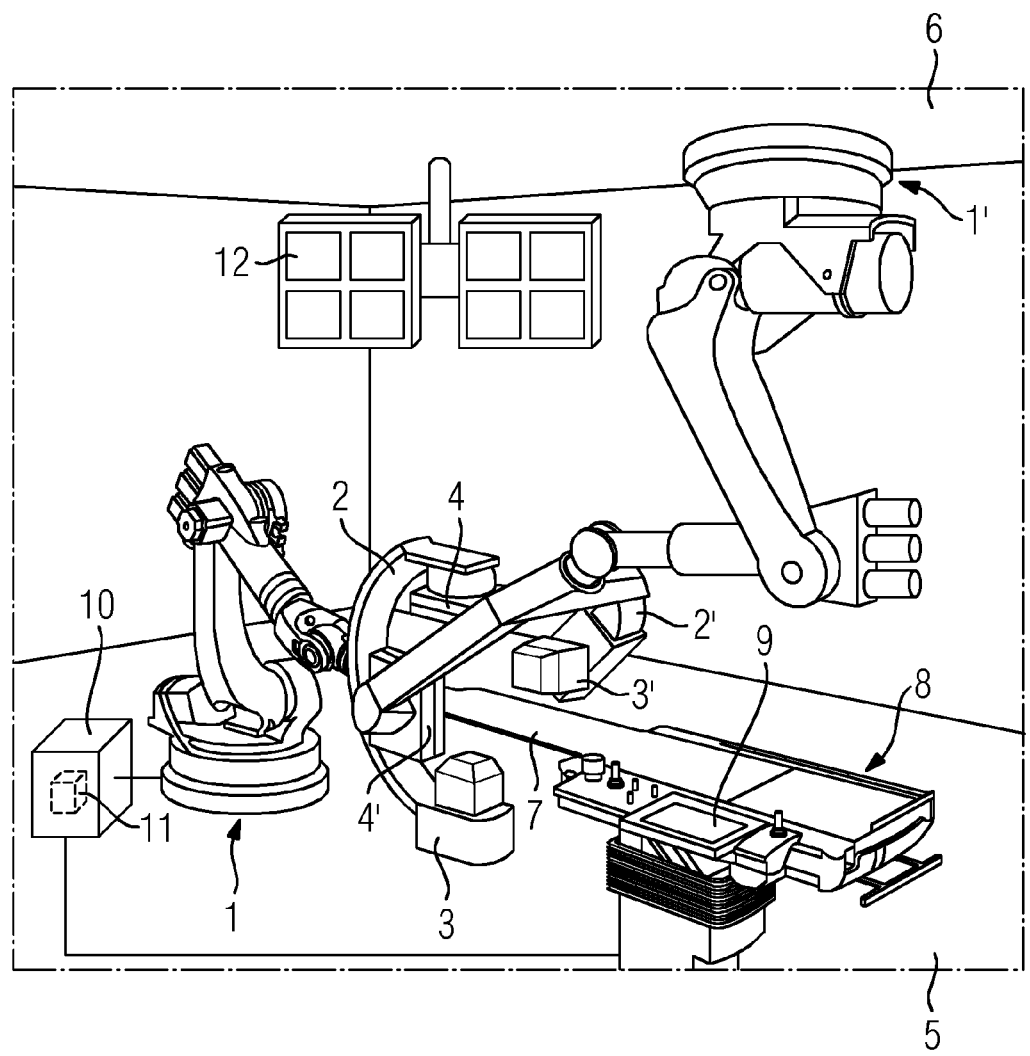
Figure 7:
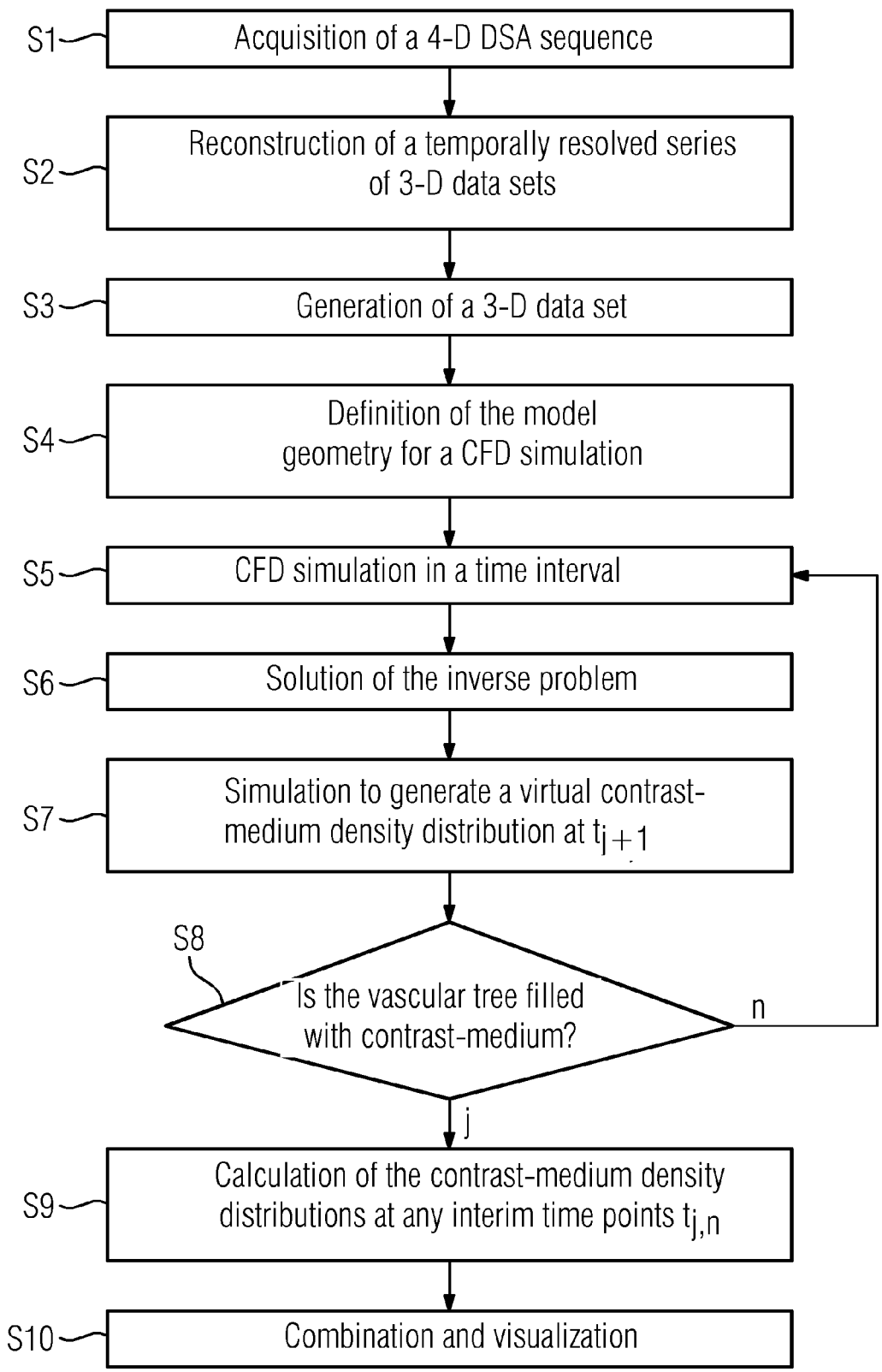
Figure 8:
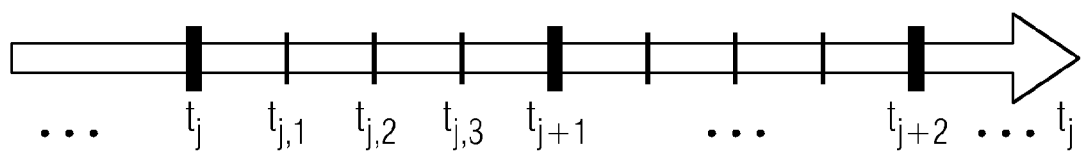

FIG. 8 describes the method steps of the angiographic examination method according to the invention for the representation of flow properties of vessels of an object under examination in more detail.

In a first method step S1, a 4-D DSA sequence for the generation of measurement-based 4-D DSA data sets is acquired.

In the second method step S2, a temporally resolved series of 3-D data sets is reconstructed for the generation of a temporal contrast-medium density distribution, which is represented as a contrast-medium density distribution that develops over time.

According to the third method step S3, a 3-D data set with complete filling with contrast medium of the vessels to be examined is generated.

In the fourth method step S4, a model geometry for a CFD simulation is determined and defined.

According to the fifth method step S5, the result is a calculation of a CFD simulation with prespecified initial boundary conditions and simulation parameters in a time interval of $t_j$ to $t_{j+1}$.

In the sixth method step S6, the contrast-medium transport for the generation of a virtual contrast-medium density distribution at the time $t_{j+1}$ is simulated.

In a seventh method step S7, the inverse problem is solved with the aid of the virtual and real contrast-medium density distribution at the times $t_j$ and $t_{j+1}$.

According to an eighth method step S8, a check is performed to see whether complete contrast-medium filling of the vascular tree has been achieved. If this is not the case, the method steps 3 and 4 are repeated in a subsequent time interval until complete contrast-medium filling of the vascular tree is achieved.

In the ninth step S9, contrast-medium density distributions are calculated at any interim time points $t_{j,n}$.

In the last method step S10, the simulated and calculated contrast-medium density distributions are combined and both visualized.

This invention is based on the idea of calculating missing information when using the 4-D DSA method with CFD. Figuratively speaking, the CFD method is used to generate further 3-D data sets in a temporally resolved series of 3-D data sets obtained by a 4-D DSA method by "interpolation in time".

The volume data sets obtained by 4-D DSA are here used as interpolation points, while the CFD method is used to determine the contrast-medium dynamics between the scanned time points $t_i$ of the interpolation points. Therefore, interpolation in time produces a higher temporal resolution of the time-dependent 3-D data sets.

This results in the following workflow:

Acquisition of a 4-D DSA sequence and reconstruction of a temporally resolved series of 3-D data sets, which represent the contrast-medium density distribution which develops over time.

Generation of a 3-D data set with complete filling and definition of the model geometry for the subsequent CFD simulation.

CFD simulation with prespecified initial boundary conditions and simulation parameters in a first time interval of $t_j$ to $t_{j+1}$ and simulation of the contrast-medium transport for the generation of a virtual, i.e. simulated contrast-medium density distribution at the time $t_{j+1}$.

Solution of the inverse problem with the aid of the virtual and real contrast-medium density distribution at the times $t_j$ and $t_{j+1}$. Here, iterative optimization enables the degrees of freedom of the CFD simulation to be adapted until, starting from the initial data belonging to the 3-D data set at the earlier time $t_j$, the CFD simulation leads to the result data belonging to the 3-D data set at the later time $t_{j+1}$.

Repetition of steps 3 and 4 in a subsequent time interval until complete contrast-medium filling of the vascular tree is achieved.

Calculation of the contrast-medium density distributions at any interim time points $t_{j,n}$.

A further refinement can consist in the optimization of the degrees of freedom in each method step of the workflow for all the time intervals calculated up to that time.

According to the invention, two completely different approaches are combined for the determination of blood flow parameters in 3-D with high temporal resolution. To this end, the use of a model-based method is proposed in order to determine time-dependent volume data sets, which, in terms of time, lie between the time-dependent volume data sets resulting from the purely measurement-based 4-D-DSA method.

The advantage is that the calculation is only performed with simplifying and generalizing model assumptions locally, that is for purposes of CFD-based interpolation over time, while globally a purely image-based or measurement-based method is used, such as, for example, 4-D DSA, which is not based on any simplifying physical and physiological assumptions since only the patient-specific image material acquired is used as input.

This principle is explained once again in the following depiction. The volume data sets at the times $t_j$ and $t_{j+1}$ marked with a thick line result from the use of the 4-D DSA method. The volume data sets marked by the thin lines lying therebetween, in terms of time, result from the use of the CFD method, which in addition to the specific vascular geometry and further blood flow parameters receive as input the contrast-medium filling level of the vessels at the times $t_j$ and $t_{j+1}$.

Alternatively, the measure described under Point 3 can also formally be understood as an iterative optimization of the CFD simulation with the aid of a plurality of measured 3-D density distributions, that is obtained using the 4-D DSA method. This enables the CFD simulation with its assumptions to be adapted more precisely to measured data and improved. The result is optimized patient-specific simulation results. Therefore, this alternative should be understood as meaning that 4-D DSA data sets are used to make the model-based CFD simulation closer to reality.

In this way it is possible, in addition to the interim time points, to generate further physical flow parameters for 4-D DSA, such as those obtained from a CFD simulation.

The invention claimed is:

1. An angiographic examination method for representation of flow properties of vessels of an object under examination, comprising:

acquiring at least one 4-D DSA sequence;

generating time-dependent volume data sets by a measurement-based 4-D DSA method based on the at least one 4-D DSA sequence;

determining time-dependent volume data sets by a model-based method using a CFD-based interpolation over time within at least one time interval from $t_j$ to $t_{j+1}$, which lie between the time-dependent volume data sets determined by the measurement-based 4-D DSA method in terms of time, wherein the measurement-based 4-D DSA method uses an object specific image acquired as input, and wherein the CFD-based interpolation over time is performed with simplifying and generalizing model assumptions;

combining the time-dependent volume data sets determined by the measurement-based 4-D DSA method and the time-dependent volume data sets determined by the model-based method; and determining the flow properties of vessels of the object based on the combined time-dependent volume data sets, wherein the combined time-dependent volume data sets is used in the examination which quantifies blood flow in the vessel with temporal resolution.

2. The angiographic examination method as claimed in claim 1, further comprising:

reconstructing a temporally resolved series of 3-D data sets based on the at least one 4-D DSA sequence for generating a temporal course of a real contrast-medium density distribution, generating a 3-D data set with a complete contrast-medium filling of the vessels to be examined, defining a model geometry for a CFD simulation, calculating the CFD simulation with prespecified initial boundary conditions and simulation parameters in at least one time interval from $t_j$ to $t_{j+1}$, simulating a contrast-medium transport for generating a virtual contrast-medium density distribution at the time $t_{j+1}$, solving an inverse problem with the virtual and the real contrast-medium density distribution at the times $t_j$ and $t_{j+1}$ of the at least one time interval, repeating steps of generating a 3-D data set and defining a model geometry in a subsequent time interval $t_{j+1}$ to $t_{j+2}$ until a complete virtual contrast-medium filling of the vessels, calculating contrast-medium density distributions at any interim time points $t_{j,n}$, and combining the simulated and the calculated contrast-medium density distributions and visualizing the combination.

3. The angiographic examination method as claimed in claim 2, wherein an iterative optimization by an adaptation of degrees of freedom of the CFD simulation is performed for solving the inverse problem, and wherein the iterative optimization starts from an initial data of the 3-D data set at an earlier time $t_j$ until the simulation in a result data of the 3-D data set at a later time $t_{j+1}$.

4. The angiographic examination method as claimed in claim 3, wherein the degrees of freedom are optimized for all time intervals calculated up to that time.

* * * * *